United States Patent [19]

Kalopissis et al.

[11] 4,045,170

[45] Aug. 30, 1977

[54] HAIR DYE COMPOSITION CONTAINING AN INDOANILINE

[75] Inventors: Gregoire Kalopissis, Paris; Andree Bugaut, Boulogne-sur-Seine; Francoise Estradier, Paris, all of France

[73] Assignee: L'Oreal, Paris, France

[21] Appl. No.: 662,964

[22] Filed: Mar. 1, 1976

Related U.S. Application Data

[60] Division of Ser. No. 580,830, May 27, 1975, Pat. No. 3,963,764, which is a continuation-in-part of Ser. No. 249,227, May 1, 1972, abandoned, which is a continuation-in-part of Ser. No. 213,750, Dec. 29, 1971, Pat. No. 3,867,094.

[30] Foreign Application Priority Data

| May 10, 1971 | Luxembourg | 63145 |
| May 10, 1971 | Luxembourg | 63144 |
| Dec. 30, 1970 | Luxembourg | 62348 |

[51] Int. Cl.$^2$ .............................................. D06P 3/08
[52] U.S. Cl. .............................................. 8/11; 8/10; 8/10.1; 8/10.2; 8/32; 260/396 N; 544/105
[58] Field of Search .................... 8/10.1, 10.2, 10, 11, 8/32; 260/396 N, 244 R

[56] References Cited

U.S. PATENT DOCUMENTS

| 2,013,394 | 9/1935 | Tolstoovhov | 260/575 |
| 2,895,826 | 7/1959 | Salminen et al. | 96/55 |
| 3,148,062 | 9/1964 | Whitmore et al. | 96/55 |
| 3,210,252 | 10/1965 | Blanke et al. | 8/10.2 |

FOREIGN PATENT DOCUMENTS

| 350,077 | 10/1905 | France | 260/396 |
| 707,705 | 4/1954 | United Kingdom | 260/396 |

OTHER PUBLICATIONS

Chemical Abstracts, vol. 24: 3944, (1930).
Vittum et al., Journal of the American Chemical Society, vol. 69, pp. 152-155, (1947).

*Primary Examiner*—Albert T. Meyers
*Assistant Examiner*—Vera C. Clarke
*Attorney, Agent, or Firm*—Cushman, Darby & Cushman

[57] ABSTRACT

A dye composition for keratinic fibers comprises an aqueous alcoholic solution of an indoaniline selected from (a) one having the formula

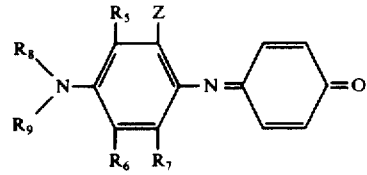

wherein Z is selected from amino, acetylamino and hydroxy; $R_5$, $R_6$ and $R_7$ each independently are selected from hydrogen, lower alkyl having 1-6 carbon atoms and lower alkoxy having 1-6 carbon atoms; $R_8$ is selected from hydrogen, lower alkyl having 1-6 carbon atoms and together with $R_5$ and the nitrogen atom to which $R_8$ is attached form dihydro-paroxazine; and $R_9$ is selected from hydrogen, lower alkyl having 1-6 carbon atoms and together with $R_6$ and the nitrogen atom to which $R_9$ is attached form dihydro-paroxazine, with the proviso that at least two of $R_5$, $R_6$, $R_7$, $R_8$ and $R_9$ are other than hydrogen when Z is $NH_2$ and that only one of $R_8$ and $R_9$ form dihydro-paroxazine; (b) an acid salt of said indoaniline in (a); and (c) a double chloride of zinc and said indoaniline in (a). When the indoaniline is employed in combination with an aqueous alcoholic solution, a hair dyeing lotion which also sets the hair is provided by the inclusion therein of a cosmetic film forming resin.

16 Claims, No Drawings

HAIR DYE COMPOSITION CONTAINING AN INDOANILINE

This is a division, of application Ser. No. 580,830 filed May 27, 1975, now U.S. Pat. No. 3,963,764, which is a continuation of Ser. No. 249,227, filed May 1, 1972, now abandoned, which is a continuation-in-part of Ser. No. 213,750, filed Dec. 29, 1971, now U.S. Pat. No. 3,867,094.

The present invention relates to a novel indoaniline having the formula

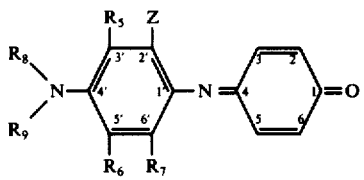

(I)

wherein Z represents a member selected from the group consisting of amino, acylamino and hydroxy; $R_5$, $R_6$ and $R_7$ each independently represent a member selected from the group consisting of hydrogen, lower alkyl having 1-6 carbon atoms and lower alkoxy having 1-6 carbon atoms; $R_8$ represents a member selected from the group consisting of hydrogen, lower alkyl having 1-6 carbon atoms, lower alkyl having 1-6 carbon atoms and substituted with a member selected from the group consisting of hydroxy, carbamoyl, acylamino and piperidinyl and together with $R_5$ and the nitrogen atom to which $R_8$ is attached form a heterocycle selected from the group consisting of dihydro-paroxazine and pyrroline; $R_9$ represents a member selected from the group consisting of hydrogen, lower alkyl having 1-6 carbon atoms, lower alkyl having 1-6 carbon atoms and substituted with a member selected from the group consisting of hydroxy, carbamoyl, acylamino and piperidinyl and together with $R_6$ and the nitrogen atom to which $R_9$ is attached form a heterocycle selected from the group consisting of dihydro-paroxazine and pyrroline, with the proviso that at least two of $R_5$, $R_6$, $R_7$, $R_8$ and $R_9$ are other than hydrogen when Z is $-NH_2$; and the salts formed by these indoanilines with organic or mineral acids, in particular, their acetates, oxalates, hydrochlorides, hydrobromides, persulfates or perchlorates; and the double chlorides of zinc of these compounds; as well as the tautomers of the compounds represented by formula I.

The indoanilines of the present invention can be prepared by three different processes described below.

METHOD 1

A first process for obtaining the indoanilines of Formula I or their salts comprises condensing a paraaminophenol having the formula

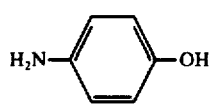

(II)

or alternatively a salt thereof, such as the hydrochloride, hydrobromide or sulfate, on a compound having the formula

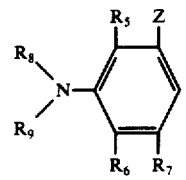

(III)

wherein $R_5$, $R_6$, $R_7$, $R_8$, $R_9$ and Z have the meaning given above, or alternatively a salt thereof such as its hydrochloride, hydrobromide or sulfate.

The reaction can be performed in an aqueous medium, an aqueous alcoholic medium or an aqueous acetonic medium, at a pH made alkaline by addition to said chosen medium of an aqueous solution of sodium, potassium or ammonium hydroxide, the pH preferably ranging from about 8 to 10 at a temperature between $-5°$ to $40°$ C and in the presence of an oxidizing agent such as air, hydrogen peroxide, ammonium persulfate or potassium ferricyanide. The indoaniline of formula I is then isolated in the form of a free base.

When an aqueous alcoholic medium is employed the alcohol can be present in amounts of about 20 to 50 percent by weight of said medium and the alcohol employed is generally a lower alkanol having 1-4 carbon atoms.

When an aqueous acetonic medium is employed, acetone can comprise about 10 to 30 weight percent of the medium.

The amount of oxidizing agent used can vary between about 1 to 5 times the stoichiometric quantity for oxidizing the paraaminophenol to the corresponding quinone-imine. This amount is preferably 1-3 moles of persulfate or 2-5 moles of ferricyanide for 1 mole of paraamino phenol.

The reaction can also be performed in an aqueous medium between $0°-20°$ C at an acid pH, preferably ranging between 1-5, and in the presence of ferric chloride in amounts of about 2 to 6 moles per mole of paraaminophenol. The indoaniline of formula I is then isolated in the form of its hydrochloride.

Representative of compounds having formula III usefully employed in accordance with the present invention are: 1,3-dimethyl 2,4-diamino benzene, N,N-dimethyl metaphenylenediamine, 6-hydroxy phenomorpholine, 6-hydroxy 4-methyl phenomorpholine,3-N,N-diethylamino phenol, 6-amino phenomorpholine, 1-ethyl 6-amino indoline, 3-acetylamino N,N-dimethylaniline, 2-methyl 5-acetylamino aniline and 3-acetylamino aniline.

Generally, the paraaminophenol and the compound represented by formula III are employed in essentially equimolar amounts.

METHOD 2

The indoanilines of formula I can also be prepared by the condensation of a quinone-chloroimide having the formula

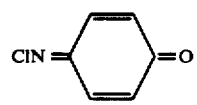

(IV)

on a compound of formula III, this condensation being performed in an aqueous medium, an aqueous alcoholic medium or an aqueous acetonic medium, also as defined above, at a temperature between 0°–40° C. Essentially equimolar amounts of the quinonechloroimide and compound III are employed.

METHOD 3 the indoanilines of formula I can also be prepared by condensing paranitrosophenol having the formula

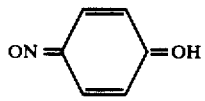

(V)

on a compound having formula III. The condensation reaction is effected in an alcohol medium in the presence of zinc chloride at the reflux temperature of the reaction medium. The indoaniline is then isolated in the form of its double zinc salt. The alcohol used for the reaction medium can be a lower alkanol having 1–4 carbon atoms and the zinc chloride is generally present in amounts effective to precipitate the desired product.

The indoanilines according to the invention and their salts constitute dyes which exhibit good dyeing power with regard to keratinic fibers and, in particular, human hair, in a pH range varying from 4 to 11. Because of their great affinity for these fibers they can be used at very slight concentrations, for instance, from about 0.002 to 0.005 percent by weight of the dye composition which explains why even salts that are only slightly soluble in water can be effectively used.

The indoanilines of the present invention make it possible to obtain a very wide range of shades, in particular purples, mauves, blues, greens, pinks, ash grays and iridescent silver grays with glints of blue or pink. All the shades have great brilliance and exhibit pearly glints which are esthetic qualities highly prized in the hair dyeing art.

Consequently, the present invention also provides a novel dyeing composition for keratinic fibers, in particular human hair, characterized by the fact that it contains in an aqueous or aqueous alcoholic solution at least a compound of formula I or a salt of this compound.

The dye compositions according to the invention can contain only the compounds of formula I, in which case they make it possible to obtain the entire range of shades, with the exception of yellows, and with application times amounting to a few minutes at ambient temperature. Certain compositions according to the invention which contain a mixture of two or three suitably chosen indoanilines make it possible to obtain ash gray as well as silver gray shades which are very luminous, and exhibit iridescent glints.

The compositions of the present invention can also contain other direct dyes, for example, anthraquinone dyes, nitro dyes of the benzene series, oxazines, azines, indophenol, indamines or indoanilines other than those of formula I.

Because of the great dyeing power of the novel compounds of formula I, their concentration in the compositions according to the invention can, as has been said above, be extremely slight, of the order of 0.002% by weight. However, this concentration can vary from 0.002 to 2% and preferably between about 0.005 to 0.5% by weight.

The dye compositions according to the invention are in the form of aqueous solutions, to which most often have been added low molecular weight alcohols such as ethanol or isopropanol, or glycols such as propylene glycol or butyl glycol, the alcohol or glycol facilitating the solution of the dye in the composition. The proportion of alcohol used is generally between 20 and 70% by weight, while the proportion of glycol is generally between 1 and 6% by weight.

The compositions according to the invention can also contain various ingredients usually employed in capillary cosmetics, for example, wetting agents, dispersing agents, swelling agents, penetrating agents, thickeners, softeners or perfumes.

The pH of the dye compositions according to the invention can vary between 4 and 11. Preferably, however, the pH ranges between 5 and 9. To regulate this pH at a desired value, it is possible to use as alkalizing agents, ammonia or an amine such as mono-, or di- or triethanolamine and as acidifying agents, acetic acid or lactic acid.

Dyeing of keratinic fibers, in particular, human hair, with the dye compositions according to the invention, can be performed in the usual way, by application of the composition to the fibers to be dyed, the composition being left in contact with the fibers for a time varying from 3 to 30 minutes. Following this application, the fibers are rinsed, and if desired, washed. Thereafter, the thus treated fibers are dried.

In another embodiment of the present invention, the novel indoanilines can be employed in the production of capillary hair-setting lotions. These lotions comprise an aqueous alcohol solution, at least one cosmetic resin and at least one indoaniline of formula I or a salt thereof. The amount of indoaniline or its salt present in the hair-setting lotion according to this invention can be extremely slight. Such an amount generally varies between 0.002 and 1% by weight and preferably between 0.002 and 0.5% by weight, of the total hair-setting lotion composition, the pH of which generally lies between 5–8.

Alcohols suitable for the preparation of the hair-setting lotions according to the invention are low molecular weight alkanols, such as ethanol or isopropanol which are present in amounts of about 20 to 70% by weight of the total hair-setting lotion composition.

Representative cosmetic resins that can be employed in the hair-setting lotions of the present invention include, for instance, polyvinylpyrrolidone having a molecular weight of 40,000–400,000, copolymer of crotonic acid and vinyl acetate, said copolymer having a molecular weight ranging from about 10,000 to 70,000, copolymer of vinylpyrrolidone and vinyl acetate, wherein the ratio of VP to VA ranges between 50–70:-50–30, said copolymer having a molecular weight ranging from about 30,000 to 200,000 and maleic anhydridebutylvinyl ether copolymers, a 1% solution of which in methylethyl ketone has a viscosity of 0.1–3.5 cps at 25° C. These resins are used in a proportion of 1 to 3% by weight of the hair-setting lotion composition.

The hair-setting lotion of the present invention can contain only the indoanilines of formula I, in which case they constitute shading compositions which make it possible to give to the hair extremely luminous glints and a highly desirable pearly or iridescent appearance.

However, the hair-setting lotions of this invention can also contain other direct dyes, for example, anthraquinone dyes, nitro dyes of the benzene series, oxazines, azines, indamines, indophenols or indoanilines other than those of formula I.

The hair-setting lotions according to the invention are usually used by application to wet hair, previously washed and rinsed, followed by rolling the hair up on curlers and drying the hair.

The following examples are intended to illustrate the various aspects of the present invention. Unless otherwise specified, all parts and percentages are by weight and all temperatures are expressed in degrees Centigrade.

EXAMPLE 1

N-[(2'-amino 4'-dimethylamino)phenyl]benzoquinone imine having the below formula is prepared as follows:

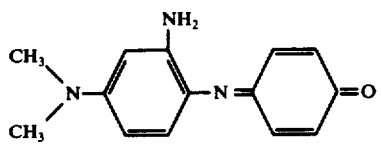

0.05 mole (5.45 g) of paraaminophenol and 0.05 mole (10.45 g) of N,N-dimethyl metaphenylene diamine dihydrochloride are introduced into 135 cc of an 0.4N solution of soda to which have been added 10 cc of ammonia at 22°Be. The resulting solution is cooled to −5° C and to it there is added, little by little, with agitation, 0.075 mole (17.10 g) of ammonium persulfate in solution in 40 cc of water to which have been added 50 cc of ammonia at 22° Be. The above reaction mixture is permitted to stand for 30 minutes at 0° C. The above indoaniline is then filtered from the reaction mass and washed with ice water. After recrystallization in a dimethylformamide-water mixture and drying under vacuum, the product is chromatographically pure and melts at 205° C.

| Analysis | Calculated for $C_{14}H_5N_3O$ | Found | |
|---|---|---|---|
| C % | 69.70 | 69.40 | 69.70 |
| H % | 6.22 | 6.33 | 6.34 |
| N % | 17.42 | 17.32 | 17.56 |

EXAMPLE 2

N-[(2'-amino 4'-dimethylamino)phenyl] benzoquinone imine described in Example 1 is prepared in accordance with Method 2 as follows:

0.05 mole (7 g) of quinonechloroimide is dissolved in 125 cc of ethanol (96° titer). Separately, 0.05 mole (10.45 g) of N,N-dimethylmetaphenylenediamine is dissolved in 120 cc of water to which have been added 5 cc of a normal soda solution and 50 cc of ammonia at 22° Be. The two solutions, preferably cooled, are then mixed together and the resulting mixture is permitted to stand for 30 minutes at 0° C. The above indoaniline precipitates therefrom in the form of crystals having a coloration that can be described as a reddish brown with golden reflections. These crystals are filtered from the reaction mass, washed with water and then recrystallized in a mixture of dimethylformamide and water. After drying under a vacuum, the indoaniline melts at 205° C and does not show any drop in its melting point when mixed with the product prepared according to Example 1.

Molecular weight calculated for $C_{14}H_{15}N_3O$ = 241.

Molecular weight found by potentiometric determination in acetic acid by perchloric acid = 240.

EXAMPLE 3

N-[(2',4'-diamino 3',5'-dimethyl)phenyl] benzoquinone imine having the below formula is prepared as follows:

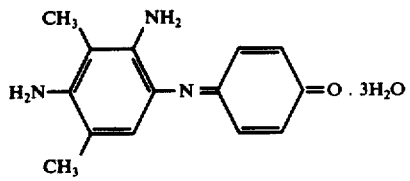

0.01 mole (1.41 g) of quinone chloroimide is dissolved in 25 cc of ethanol, 96° titer. Separately, 0.01 mole (2.09 g) of 2,6-dimethyl metaphenylenediamine dihydrochloride is dissolved in 10 cc of water to which have been added 5 cc of ammonia at 22°Be. The two solutions, preferably cooled, are mixed together and the resulting mixture is permitted to stand for 20 minutes at 0° C. The above indoaniline precipitates in the form of crystals and the precipitate is filtered therefrom. The thus recovered crystals are washed with water, then with alcohol and dried in air.

Molecular weight calculated for $C_{14}H_{15}N_3O.3H_2O$ = 295.

Molecular weight found by potentiometric determination in acetic acid by perchloric acid = 293.

| Analysis | Calculated for $C_{14}H_{15}N_3O . 3H_2O$ | Found | |
|---|---|---|---|
| C % | 56.93 | 57.17 | 57.28 |
| H % | 7.17 | 6.96 | 7.0 |
| N % | 14.23 | 14.23 | 14.36 |

EXAMPLE 4

N-[(2'-acetylamino 4'-amino)phenyl]benzoquinone imine having the below formula is prepared as follows:

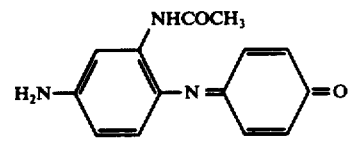

0.01 mole (1.86 g) of 3-acetylamino aniline hydrochloride and 0.01 mole (1.09 g) of paraamino phenol are dissolved in a 0.2N hydrochloric acid solution. To this solution, preferably cooled to 0° C, there are added, little by little with agitation, 24 cc of a 28% ferric chloride solution. The resulting reaction mixture is permitted to stand for 10 minutes at −10° C and the resulting above indoaniline precipitates therefrom in the form of its hydrochloride. After filtering the said precipitate, it is washed with a little ice water, then with acetone and dried under a vacuum. The above indoaniline melts with decomposition at 225° C.

Molecular weight calculated for $C_{14}H_{13}N_3O_2.HCL$ = 291.5.

Molecular weight found by potentiometric determination in water by a 0.1N soda solution = 294.

3 g of the thus obtained indoaniline in hydrochloride form are dissolved in 200 cc of ice water. The above solution is then alkalinized to a pH of 7 by adding thereto ammonia at 22° Be. The desired indoaniline precipitates in the form of green crystals which are filtered, washed with water and recrystallized in acetone. After drying the same under vacuum, the product melts at 214° C.

Molecular weight calculated for $C_{14}H_{13}N_3O_2 = 255$.

Molecular weight found by potentiometric determination in acetic acid by perchloric acid = 254.

| Analysis | Calculated for $C_{14}H_{13}N_3O_2$ | Found | |
|---|---|---|---|
| C % | 65.87 | 65.49 | 65.27 |
| H % | 5.10 | 5.11 | 5.08 |
| N % | 16.47 | 16.32 | 16.28 |

EXAMPLE 5

The monohydrochloride, monohydrate of N[(2'-acetylamino 4'-amino 5'-methyl)phenyl]benzoquinone imine having the below formula is prepared as follows:

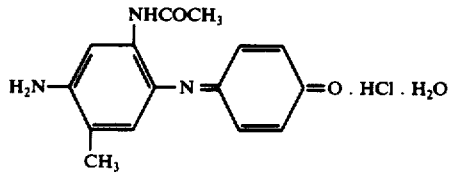

0.01 mole (1.64 g) of 2-amino 4-acetylamino toluene and 0.01 mole (1.09 g) of paraaminophenol are dissolved in 25 cc of normal hydrochloric acid solution. To this solution, preferably cooled to 0° C, there are added, little by little with agitation, 18 cc of a 28% ferric chloride solution. The resulting mixture is permitted to stand for 10 minutes at 0° C. The above indoaniline precipitates and is filtered therefrom. After washing with a 50% aqueous acetone solution and drying on potassium, the product is chromatographically pure and melts with decomposition between 225° and 230° C.

Molecular weight calculated for $C_{15}H_{15}N_3O_2.HCl.H_2O = 323.5$.

Molecular weight found by potentiometric determination in water by 0.1N soda solution = 316.

| Analysis | Calculated for $C_{15}H_{15}N_3O_2 . HCl . H_2O$ | Found | |
|---|---|---|---|
| C % | 55.63 | 55.35 | 55.27 |
| H % | 5.56 | 5.44 | 5.52 |
| N % | 12.98 | 12.89 | 12.92 |

EXAMPLE 6

The monohydrochloride, monohydrate of N[(2'-acetylamino 4'-dimethylamino)phenyl]benzoquinone imine having the below formula is prepared as follows:

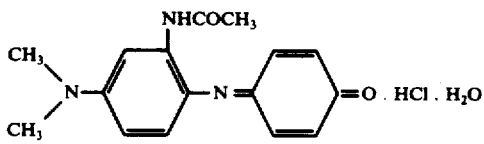

0.01 mole (1.09 g) of paraaminophenol and 0.01 mole (1.78 g) of 3-acetylamino dimethylaniline are dissolved in 25 cc of a 0.4N hydrochloric acid solution. To this solution, preferably cooled to 0° C, there are added, little by little with agitation, 15 cc of a 28% ferric chloride solution. The resulting mixture is permitted to stand for 10 minutes at −10° C. The above indoaniline precipitates and is filtered therefrom. After washing the precipitate with a little ice water and then with acetone and drying under a vacuum, the product melts with decomposition at 170° C.

Molecular weight calculated for $C_{16}H_{17}N_3O_2.HCl.H_2O = 337.5$.

Molecular weight found by potentiometric determination in water by a 0.1N soda solution = 334.

| Analysis | Calculated for $C_{16}H_{17}N_3O_2 . HCl . H_2O$ | Found | |
|---|---|---|---|
| C % | 56.88 | 56.75 | 56.88 |
| H % | 5.93 | 6.01 | 5.89 |
| N % | 12.44 | 12.30 | 12.46 |

EXAMPLE 7

N-[(6'-amino 1'-oxa 4'-aza 1', 2', 3', 4'-tetrahydro) 7'-naphthyl] benzoquinone imine having the below formula is prepared as follows:

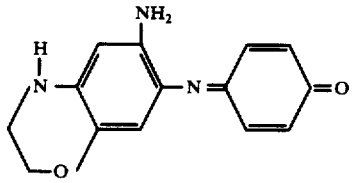

0.05 mole (1.10 g) of 6-amino phenomorpholine dihydrochloride and 0.005 mole (0.55 g) of paraaminophenol are dissolved in 25 cc of a 0.2N hydrochloric acid solution. To the resulting solution, cooled to 0° C, there are added, little by little, 12 cc of a 28% solution of ferric chloride. The hydrochloride of the above indoaniline precipitates immediately and is then filtered from the reaction mass, washed with a little normal hydrochloric acid solution and then with a little ice water. The product is chromatographically pure and melts with decomposition at 180° C.

Molecular weight calculated for $C_{14}H_{13}N_3O_2.HCl = 291.5$.

Molecular weight found by potentiometric determination in water with a 0.1N soda solution = 294.

0.8 g of the thus obtained indoaniline in hydrochloride form is dissolved in 50 cc of water. The above solution is then alkalinized to a pH of 8 by adding thereto ammonia at 22° Be. The desired indoaniline precipitates in the form of flakes having a coloration that can be described as reddish brown with golden reflections, which flakes are filtered, washed with water and dried under a vacuum. The resulting product is chromatographically pure and melts at 165° C.

| Analysis | Calculated for $C_{14}H_{13}N_3O_2$ | Found | |
|---|---|---|---|
| C % | 65.88 | 65.57 | 65.61 |
| H % | 5.10 | 5.09 | 5.09 |
| N % | 16.48 | 16.38 | 16.43 |

EXAMPLE 8

The double chloride of zinc and N[(6'-amino 1'-oxa 4'-methyl 4'-aza 1',2',3',4'-tetrahydro) 7'-naphthyl] benzoquinone imine having the below formula is prepared as follows:

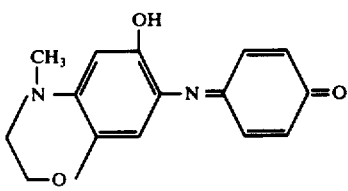

In 15 cc of absolute ethyl alcohol, there are introduced 0.01 mole (1.65 g) of 6-hydroxy 4-methyl phenomorpholine and 0.01 mole (1.23 g) of paranitrosophenol as well as 1.5 g of anhydrous zinc chloride. The resulting reaction mixture is heated with agitation for 30 minutes at reflux. The above indoaniline precipitates and is filtered therefrom. After washing with ethanol, the thus recovered product is chromatographically pure.

EXAMPLE 9

The double chloride of zinc and N-[(4'-diethylamino 2'-hydroxy)phenyl]benzoquinone imine having the below formula is prepared as follows:

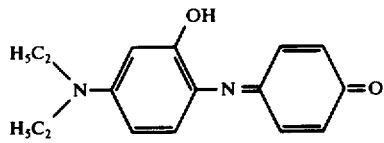

In 20 cc of absolute ethanol there are introduced 0.01 mole (1.65 g) of N,N-3-diethylamino phenol and 0.01 mole (1.23 g) of paranitrosophenol as well as 1.5 g of anhydrous zinc chloride. The resulting reaction mixture is heated with agitation for 30 minutes at reflux. The above indoaniline precipitates and is filtered therefrom. After washing with ethanol, the thus recovered product is chromatographically pure.

EXAMPLE 10

The following hair-setting lotion composition is prepared:

| | |
|---|---|
| Dye of Example 1 | 0.05 g |
| Vinyl acetate-crotonic acid copolymer (Vinyl acetate 90% — crotonic acid 10%, molecular wt 45,000–50,000) | 2 g |
| Ethyl alcohol, 96° titer, q.s.p. for 50° | |
| Water, q.s.p. | 100 g |
| Ammonia, 22° Be', q.s.p. | pH 8 |

This hair-setting lotion composition when applied to bleached hair imparts thereto a light pearly parme shade.

EXAMPLE 11

The following dye composition is prepared:

| | |
|---|---|
| Dye of Example 1 | 0.10 g |
| Butyl gylcol | 5 g |
| Lauryl alcohol oxyethylenated with 10.5 moles ethylene oxide | 5 g |
| Water, q.s.p. | 100 g |
| Ammonia, 22° Be', q.s.p. | pH 7.5 |

This dye composition when applied to bleached hair for 10 minutes at 20° C imparts thereto after rinsing and shampooing a very deep purple shade.

EXAMPLE 12

The following hair-setting lotion composition is prepared:

| | |
|---|---|
| Dye of Example 1 | 0.025 g |
| Nitro orthophenylene diamine | 0.05 g |
| Vinylacetate-crotonic acid copolymer (as in Example 10) | 2 g |
| Ethyl alcohol 96° titer, q.s.p. 50° | |
| Water, q.s.p. | 100 g |
| Triethanolamine, q.s.p. | pH 7 |

This hair-setting lotion composition when applied to bleached hair imparts thereto a pearly blond shade with mauve glints.

EXAMPLE 13

The following dye composition is prepared:

| | |
|---|---|
| Dye of Example 4 | 0.1 g |
| Ethyl alcohol | 25 g |
| Water, q.s.p. | 100 g |
| Ammonia, 22° Be, q.s.p. | pH 10 |

This dye composition when applied for 20 minutes at ambient temperature to 95% naturally white hair, imparts thereto, after rinsing and shampooing a pale silvery pink shade.

EXAMPLE 14

The following hair-setting lotion composition is prepared:

| | |
|---|---|
| Dye of Example 4 | 0.05 g |
| Vinyl acetate-crotonic acid copolymer (as in Example 10) | 2 g |
| Ethyl alcohol, 96° titer, q.s.p. 50° | |
| Water, q.s.p. | 100 g |
| Triethanolamine, q.s.p. | pH 7 |

This hair-setting lotion composition when applied to bleached hair, imparts thereto a rose or pink shade with golden glints.

EXAMPLE 15

The following hair-setting lotion composition is prepared:

| | |
|---|---|
| Dye of Example 5 in the form of its hydrochloride | 0.025 g |
| Vinyl acetate-crotonic acid copolymer (as in Example 10) | 2 g |
| Ethyl alcohol, 96° titer, q.s.p. 50° | |
| Water, q.s.p. | 100 g |
| Ammonia, 22° Be, q.s.p. | pH 6 |

This hair-setting lotion composition when applied to bleached hair imparts thereto a pearly light blue shade.

EXAMPLE 16

The following dye composition is prepared:

| Dye of Example 5 in the form of its | |
|---|---|
| hydrochloride | 0.025 g |
| Water, q.s.p. | 100 g |
| Ammonia, 22° Be, q.s.p. | pH 4.5 |

This dye composition when applied to bleached hair for 10 minutes at ambient temperature, imparts thereto after rinsing and shampooing a very luminous blue shade.

EXAMPLE 17

The following hair-setting lotion composition is prepared:

| Dye of Example 5 | 0.06 g |
|---|---|
| N-[(4'-hydroxy)phenyl]2,6-dimethyl benzoquinone imine | 0.05 g |
| Vinyl acetate-crotonic acid copolymer (as in Example 10) | 2 g |
| Ethyl alcohol, 96° titer, q.s.p. 50° | |
| Water, q.s.p. | 100 g |
| Triethanolamine, q.s.p. | pH 7 |

This hair-setting lotion composition when applied to bleached hair imparts thereto a silvery blue gray shade.

EXAMPLE 18

The following hair-setting lotion composition is prepared:

| Dye of Example 5 in the form of its hydrochloride | 0.025 g |
|---|---|
| Dye of Example 3 | 0.025 g |
| Vinyl acetate-crotonic acid copolymer (as in Example 10) | 2 g |
| Ethyl alcohol, 96° titer, q.s.p. 50° | |
| Water, q.s.p. | 100 g |
| Triethanolamine, q.s.p. | pH 7 |

This hair-setting lotion when applied to bleached hair imparts thereto a silver gray shade.

EXAMPLE 19

The following dye composition is prepared:

| Dye of Example 6 | 0.2 g |
|---|---|
| Butyl glycol | 5 g |
| Lauryl alcohol oxyethylenated with 10.5 moles of ethylene oxide | 5 g |
| Water, q.s.p. | 100 g |
| Ammonia, 22° Be, q.s.p. | pH 7 |

This dye composition when applied for 5 minutes at 20° C to 95% naturally white hair imparts thereto, after rinsing and shampooing, an almond green shade.

EXAMPLE 20

The following dye composition is prepared:

| Dye of Example 7 | 0.1 g |
|---|---|
| Butyl glycol | 5 g |
| Lauryl alcohol oxyethylenated with 10.5 moles ethylene oxide | 5 g |
| Water, q.s.p. | 100 g |
| Ammonia, 22° Be, q.s.p. | pH 8 |

This dye composition when applied for 20 minutes at ambient temperature to 95% naturally white hair imparts thereto, after rinsing and shampooing, a silvery green shade.

EXAMPLE 21

The following dye composition is prepared:

| Dye of Example 7 | 0.005 g |
|---|---|
| Butyl glycol | 5 g |
| Lauryl alcohol oxyethylenated with 10.5 moles ethylene oxide | 5 g |
| Water, q.s.p. | 100 g |
| Ammonia, 22° Be, q.s.p. | pH 4.5 |

This dye composition when applied for 10 minutes at ambient temperature to bleached hair imparts thereto, after rinsing and shampooing a pearly shade with pale green glints.

EXAMPLE 22

The following hair-setting lotion composition is prepared:

| Dye of Example 8 in the form of its hydrochloride | 0.05 g |
|---|---|
| Vinyl acetate-crotonic acid copolymer (as in Example 10) | 2 g |
| Ethyl alcohol, 96° titer, q.s.p. 50° | |
| Water, q.s.p. | 100 g |
| Triethanolamine, q.s.p. | pH 8 |

This hair-setting lotion composition when applied to bleached hair imparts thereto a very luminous pearly rose shade.

EXAMPLE 23

The following hair-setting lotion composition is prepared:

| Dye of Example 9 | 0.05 g |
|---|---|
| Vinyl acetate-crotonic acid copolymer (as in Example 10) | 2 g |
| Ethyl alcohol, 96° titer, q.s.p. 50° | |
| Water, q.s.p. | 100 g |
| Triethanolamine, q.s.p. | pH 7 |

This hair-setting lotion composition when applied to bleached hair imparts thereto a rose shade with golden glints.

EXAMPLE 24

The following dye composition is prepared:

| Dye of Example 1 | 0.01 g |
|---|---|
| Dye of Example 7 | 0.05 g |
| Butyl glycol | 5 g |
| Lauryl alcohol oxyethylenated with 10.5 moles ethylene oxide | 5 g |
| Water, q.s.p. | 100 g |
| Ammonia, 22° Be, q.s.p. | pH 8 |

This dye composition when applied for 15 minutes at ambient temperature to 95% naturally white hair imparts thereto, after rinsing and shampooing, a silver gray shade.

EXAMPLE 25

The following dye composition is prepared:

| Dye of Example 6 | 0.1 g |
|---|---|
| Trihydrate of N-[(2',4'-diamino 5'-methyl) phenyl]benzoquinone imine | 0.025 g |
| Water, q.s.p. | 100 g |
| Ammonia, 22° Be, q.s.p. | pH 8.5 |

This dye composition when applied for 10 minutes at ambient temperature to 95% naturally white hair imparts thereto, after rinsing and shampooing, a pale, silvery blue gray shade.

EXAMPLE 26

The following hair-setting lotion composition is prepared:

| | |
|---|---|
| Dye of Example 9 | 0.05 g |
| Vinyl acetate-crotonic acid copolymer (as in Example 10) | 1 g |
| Ethyl alcohol, 96° titer, q.s.p. 25° | |
| Water, q.s.p. | 100 g |
| Triethanolamine, q.s.p. | pH 6 |

This hair-setting lotion composition when applied to bleached hair imparts thereto a rose violet shade.

EXAMPLE 27

The following dye composition is prepared:

| | |
|---|---|
| Dye of Example 7 | 0.05 g |
| N-[(2',4'-diamino 5'-methoxy)phenyl] 2-chloro benzoquinone imine | 0.01 g |
| N-[(2',4'-diamino)phenyl]benzoquinone imine hydrochloride | 0.01 g |
| Butyl glycol | 5 g |
| Lauryl alcohol oxyethylenated with 10.5 moles ethylene oxide | 5 g |
| Ammonia, 22° Be, q.s.p. | pH 9 |
| Water, q.s.p. | 100 g |

This dye composition when applied for 10 minutes at ambient temperature to 95% naturally white hair imparts thereto, after rinsing and shampooing, an ash gray shade.

EXAMPLE 28

The following hair-setting lotion is prepared:

| | |
|---|---|
| Dye of Example 7 | 0.4 g |
| Vinyl acetate-crotonic acid copolymer (as in Example 10) | 2 g |
| Ethyl alcohol, 96° titer, q.s.p. 50° | |
| Water, q.s.p. | 100 g |
| Triethanolamine, q.s.p. | pH 5.5 |

This hair-setting lotion composition when applied to bleached hair imparts thereto a deep turquoise blue shade.

What is claimed is:

1. A dye composition for keratinic fibers comprising an aqueous or aqueous alcoholic solution of an indoaniline selected from the group consisting of (a) an indoaniline having the formula

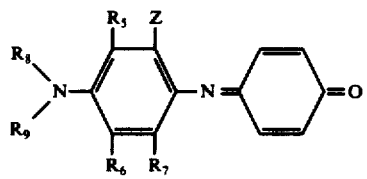

wherein Z is selected from the group consisting of amino, acetylamino and hydroxy; $R_5$, $R_6$ and $R_7$ each independently are selected from the group consisting of hydrogen, lower alkyl having 1-6 carbon atoms and lower alkoxy having 1-6 carbon atoms; $R_8$ is selected from the group consisting of hydrogen, lower alkyl having 1-6 carbon atoms and together with $R_5$ and the nitrogen atom to which $R_8$ is attached form dihydro-paroxazine; and $R_9$ is selected from the group consisting of hydrogen, lower alkyl having 1-6 carbon atoms and together with $R_6$ and the nitrogen atom to which $R_9$ is attached form dihydro-paroxazine, with the proviso that at least two of $R_5$, $R_6$, $R_7$, $R_8$ and $R_9$ are other than hydrogen when Z is $NH_2$ and that only one of $R_8$ and $R_9$ form dihydro-paroxazine;

b. an acid salt of said indoaniline in (a); and c. a double chloride of zinc and said indoaniline in (a); said indoaniline being present in an amount effective to color said fibers.

2. The dye composition of claim 1 wherein said indoaniline is present in an amount of 0.002-2 percent by weight of said composition.

3. The dye composition of claim 1 having a pH ranging between 4-11.

4. The dye composition of claim 1 wherein said aqueous alcoholic solution is an aqueous solution of a low molecular weight alkanol werein said alkanol is present in an amount of 20-70 weight percent of said composition.

5. The dye composition of claim 4 wherein said low molecular weignt alkanol is selected from the group consisting of ethanol and isopropanol.

6. The dye composition of claim 1 which also includes a glycol present in an amount of 1-6 weight percent of said composition.

7. The dye composition of claim 6 wherein said glycol is selected from the group consisting of propylene glycol ad butyl glycol.

8. The dye composition of claim 1 which also includes a dye selected from the group consisting of a nitrobenzene dye, an indophenol and an indoaniline other than that defined in claim 1.

9. The dye composition of claim 1 wherein said indoaniline is selected from the group consisting of
N-[(2'-amino-4'-dimethylamino)phenyl] benzoquinone imine,
N-[(2',4'-diamino-3',5'-dimethyl)phenyl] benzoquinone imine,
N-[(2'-acetylamino-4'-amino)phenyl] benzoquinone imine,
N-[(2'-acetylamino-4'-amino-5'-methyl)phenyl] benzoquinone imine hydrochloride,
N-[(2'-acetylamino-4'-dimethylamino)phenyl] benzoquinone imine hydrochloride,
N[(6'-amino-1'-oxa-4'-aza-1',2',3',4'-tetrahydro) 7'-naphthyl] benzoquinone imine,
the double chloride of zinc and N-[(6'-amino-1'-oxa-4'-methyl-4'-aza-1',2',3',4'-tetrahydro) 7'-naphthyl] benzoquinone imine, and
the double chloride of zinc and N-[(4'-diethyl-amino-2'-hydroxy)phenyl]benzoquinone imine.

10. The dye composition of claim 1 wherein said indoaniline is N-[(2',4'-diamino-3',5'-dimethyl)phenyl] benzoquinone imine.

11. A process for dyeing keratinic fibers comprising impregnating said fibers to be dyed with the composition of claim 1 in an amount effective to dye said fibers, permitting said composition to remain in contact with said fibers for a period ranging from about 3 to 30 minutes, rinsing said fibers and drying said fibers.

12. A hair dyeing composition comprising in an aqueous solution of a lower alkanol an indoaniline selected from the group consisting of (a) an indoaniline having the formula

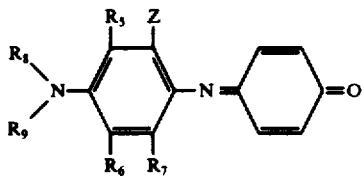

wherein Z is selected from the group consisting of amino, acetylamino and hydroxy; $R_5$, $R_6$ and $R_7$ each independently are selected from the group consisting of hydrogen, lower alkyl having 1-6 carbon atoms and lower alkoxy having 1-6 carbon atoms; $R_8$ is selected from the group consisting of hydrogen, lower alkyl having 1-6 carbon atoms and together with $R_5$ and the nitrogen atom to which $R_8$ is attached form dihydro-paroxazine; and $R_9$ is selected from the group consisting of hydrogen, lower alkyl having 1-6 carbon atoms and together with $R_6$ and the nitrogen atom to which $R_9$ is attached form dihydro-paroxazine, with the proviso that at least two of $R_5$, $R_6$, $R_7$, $R_8$ and $R_9$ are other than hydrogen when Z is $NH_2$ and that only one of $R_8$ and $R_9$ form dihydro-paroxazine;

b. an acid salt of said indoaniline in (a); and
c. a double chloride of zinc and said indoaniline in (a);
and a cosmetic film forming resin, said indoaniline being present in an amount effective to dye said hair and said cosmetic film forming resin being present in an amount of about 1 to 3 percent by weight of said composition.

13. The hair dyeing composition of claim 12 containing from about 0.002 to 1% by weight of said indoaniline.

14. The hair dyeing composition of claim 12 having a pH between 5-8.

15. The hair dyeing composition of claim 12 wherein said cosmetic film forming resin is selected from the group consisting of polyvinylpyrrolidone, a copolymer of vinyl acetate and crotonic acid, a copolymer of vinylpyrrolidone and vinyl acetate and a copolymer of maleic anhydride and butylvinyl ether.

16. A process for dyeing hair comprising washing and rinsing said hair, applying to said washed and rinsed hair the hair dyeing compositions of claim 12 in an amount effective to dye said hair, rolling said hair on curlers and drying said hair.

* * * * *